(12) United States Patent
Pressman et al.

(10) Patent No.: US 7,018,352 B2
(45) Date of Patent: Mar. 28, 2006

(54) MODULAR ANKLE-FOOT ORTHOSIS

(76) Inventors: Martin M. Pressman, 109 N. Racebrook Rd., Woodbridge, CT (US) 06525; Michael Burns, P.O. Box 122, Bellvue, CO (US) 80512

( * ) Notice: Subject to any disclaimer, the term of this patent is extended or adjusted under 35 U.S.C. 154(b) by 384 days.

(21) Appl. No.: 10/444,118

(22) Filed: May 23, 2003

(65) Prior Publication Data

US 2004/0236259 A1    Nov. 25, 2004

(51) Int. Cl.
*A61F 5/00* (2006.01)

(52) U.S. Cl. ............... 602/27; 602/23; 602/28; 602/62

(58) Field of Classification Search ............ 602/27, 602/23, 28, 29, 60, 61, 62, 65, 66; 128/869, 128/882, DIG. 15; 623/27, 28, 29, 47; 2/22
See application file for complete search history.

(56) References Cited

U.S. PATENT DOCUMENTS

| | | | |
|---|---|---|---|
| 4,289,122 A | | 9/1981 | Mason et al. |
| 4,446,856 A | | 5/1984 | Jordan |
| 4,517,968 A | * | 5/1985 | Greene et al. ........ 602/27 |
| 4,569,001 A | | 2/1986 | Brown |
| 4,587,962 A | * | 5/1986 | Greene et al. ........ 602/27 |
| 4,602,627 A | | 7/1986 | Vito et al. |
| 4,646,726 A | * | 3/1987 | Westin et al. ........ 602/27 |
| 4,688,559 A | | 8/1987 | Vito et al. |
| 4,966,134 A | | 10/1990 | Brewer |
| 5,044,360 A | * | 9/1991 | Janke ............... 623/47 |
| 5,121,742 A | | 6/1992 | Engen |
| 5,593,383 A | | 1/1997 | DeToro |
| 5,865,778 A | * | 2/1999 | Johnson ............ 602/27 |
| 5,887,591 A | | 3/1999 | Powell et al. |
| 5,897,515 A | * | 4/1999 | Willner et al. ........ 602/27 |
| 5,944,679 A | | 8/1999 | DeToro |
| 6,146,344 A | | 11/2000 | Bader |
| 6,146,349 A | * | 11/2000 | Rothschild et al. ........ 602/27 |
| 6,409,695 B1 | | 6/2002 | Connelly |
| 6,676,618 B1 | * | 1/2004 | Andersen ............. 128/882 |
| 6,689,081 B1 | * | 2/2004 | Bowman ............. 602/27 |
| 6,887,213 B1 | * | 5/2005 | Smits ................ 602/27 |

FOREIGN PATENT DOCUMENTS

| | | |
|---|---|---|
| EP | 195186 | 9/1986 |
| GB | 2101894 | 1/1983 |

* cited by examiner

*Primary Examiner*—Henry Bennett
*Assistant Examiner*—Amanda Wieker
(74) *Attorney, Agent, or Firm*—Richard C. Litman (57) ABSTRACT

A modular ankle-foot orthosis includes a lower leg and ankle support and a plantar foot support. The two components may be secured together to provide more complete support for a patient, as required. The two supports may be attached in various ways, such as a bottom heel clip extending from the foot support component, which secures through a passage in the heel of the lower leg and ankle support component. A tongue extends from the foot support clip, to capture the material at the edge of the lower leg and ankle support passage between the tongue and the foot support plate. The two components are quickly and easily assembled together and disassembled as required, to provide more versatile treatment for the patient. The complete structure, or any components thereof, is sufficiently thin to allow wear within a conventional walking shoe or the like.

19 Claims, 5 Drawing Sheets

MODULAR ANKLE-FOOT ORTHOSIS

BACKGROUND OF THE INVENTION

1. Field of the Invention

The present invention relates generally to orthopedic and orthotic braces and supports, and more specifically to a modular orthotic device or orthosis which selectively serves as an ankle and foot brace or support when the two components are assembled together, or as a foot support when the plantar support component is used separately.

2. Description of the Related Art

A number of conditions exist which adversely affect the foot and ankle of the human body. As a result, the medical fields of podiatry and chiropody have been developed in response to the various ailments and problems which can occur with the feet, or more generally with the lower extremities of the legs. A number of the various ailments and problems which can occur with the feet and lower extremities respond well to treatment using various braces, supports, and other orthotic devices. Accordingly, a number of braces, supports, and similar devices have been developed in the past for the treatment of various foot and ankle problems. A problem which occurs consistently with the various devices of the prior art, is that they tend to be relatively specialized and limited in their versatility. A medical professional treating various foot and ankle problems is thus required to have a relatively wide array of different braces, splints, and supports on hand.

The present inventors are well aware of a number of these devices, and as a result have developed a more versatile, modular ankle-foot orthosis adaptable for use in the treatment of a wide variety of ankle and foot problems. The present ankle-foot orthosis enables the medical professional to prescribe treatment of certain infirmities using only the plantar support portion, if so desired, for the correction of foot problems where required. More importantly, the present modular orthosis enables the two major components to be assembled together to provide a more extensive orthosis for the patient requiring such treatment, with the ankle and lower leg orthosis and foot orthosis portions providing limited motion between the two components. Yet, the entire assembly (or its components) is sufficiently thin to allow for wear within a shoe, boot, or the like. The versatility provided by the present modular orthosis, greatly expands the number of applications of the present invention.

A discussion of the related art of which the present inventors are aware, and its differences and distinctions from the present invention, is provided below.

U.S. Pat. No. 4,289,122 issued on Sep. 15, 1981 to Randy D. F. Mason et al., titled "Ankle-Foot Orthosis," describes an articulated orthosis serving to brace the lower leg or calf, the ankle, and the foot. The Mason et al. orthosis essentially comprises two components, i.e., a calf and ankle brace portion and a plantar foot and heel brace portion. The two portions are permanently secured to one another by means of lateral rivets or the like and cannot be separated for modular use, as can the components of the present orthosis. Plantar flexion, i.e., extension of the angle between the foot and shin of the user, is limited by means of a shoulder formed in the lower rear edge of the upper portion of the device, which serves as a stop to preclude excessive extension of the plantar portion. Only a single attachment strap is provided to extend from the calf portion of the Mason et al. device, around the upper shin. No over-ankle attachment strap is provided by Mason et al., whereas at least the lower leg and ankle portion of the present orthosis includes such an over-ankle attachment strap for more secure attachment to the patient.

U.S. Pat. No. 4,446,856 issued on May 8, 1984 to R. Paul Jordan, titled "Orthotic Device," describes a rigid, boot-like ankle and foot orthosis which completely encases and surrounds the lower leg from a point just above the ankle, extending distally to encase the foot to a point just above the toes. A thick, rigid sole platform is provided, with the sole platform having an upturned forward end to simulate the dorsiflexion of the toes during walking. The required thickness of the sole platform in order to provide the upturned forward end while allowing the toes of the wearer to extend straight, precludes wearing the Jordan orthosis within a shoe or the like. Moreover, the essentially monolithic nature of the sole platform and upward extending ankle brace precludes disassembly for modular use.

U.S. Pat. No. 4,602,627 issued on Jul. 29, 1986 to Raymond P. Vito et al., titled "Cable Controlled Orthopedic Leg Brace," describes an articulated leg brace, having hinged or pivoted hip and knee joints. The Vito et al. assembly is considerably more extensive than the present orthosis, and includes waist, thigh, and calf attachment straps. While the Vito et al. device also includes a plantar foot and ankle support portion, the foot and ankle support comprises a one-piece unit which is permanently and immovably affixed to the two distal lower leg braces, and cannot be separated therefrom.

U.S. Pat. No. 4,688,559 issued on Aug. 25, 1987 to Raymond P. Vito et al., titled "Orthopedic Leg Brace With Cable Control," describes multiple embodiments of a device related to that of their '627 U.S. Patent, discussed immediately above. The device of the '559 U.S. Patent lacks the waist strap or belt attachment of their earlier patented device. However, one embodiment includes an articulated heel and foot orthosis portion, with the plantar heel and foot support pivotally attached laterally to the lower ends of the lower leg brace portion of the device. While Vito et al. state that the device may be disassembled to repair or replace components, they are referring only to the elongate upper brace elements, rather than to the heel and foot orthosis; those components appear to be permanently assembled to one another.

U.S. Pat. No. 4,869,001 issued on Sep. 26, 1989 to Dennis N. Brown, titled "Boot And Ankle Orthotic For A Skate Boot Or The Like, And Method," describes a series of embodiments of a device or assembly configured for installation within a shoe or boot. While the device is primarily directed to use within an ice skating boot, other embodiments are provided as well. However, each of the embodiments includes a plantar support portion which is permanently attached to an ankle support portion. The ankle support portion does not extend up the leg to any great degree, and covers only the Achilles tendon area of the ankle. No positive attachment means is provided, as the shoe or boot serves to secure the device against the ankle and foot. While additional plantar attachments are also provided by Brown, these plantar components fit beneath the plantar portion of the primary structure, rather than serving as a component which may be worn separately from the ankle support portion.

U.S. Pat. No. 4,966,134. issued on Oct. 30, 1990 to Jeffrey L. Brewer, titled "Ankle Protector," describes a pair of laterally opposed plates which sandwich the ankle therebetween, to limit lateral flexing of the ankle and foot. The open forward, bottom, and rearward areas of the Brewer device allow dorsiflexion and plantar flexion of the foot, unlike the limited motion permitted by the present orthosis. Brewer does not provide any integral hind foot support or removable plantar orthotic component in his ankle protector.

U.S. Pat. No. 5,121,742 issued on Jun. 16, 1992 to Thorkild J. Engen, titled "Lower Extremity Orthotic Device," describes an upper and lower leg brace which is articulated at the knee. The lower portion of the device is a rigid, monolithic component which encircles the calf and extends as a plantar support beneath the foot. No over-ankle strap is provided in the Engen device, nor does Engen provide for the removal of the plantar support portion from the calf and ankle support portion to provide modular construction, as is the case with the present modular ankle-foot orthotic device.

U.S. Pat. No. 5,593,383 issued on Jan. 14, 1997 to William DeToro, titled "Securing Apparatus For An Ankle And Foot Orthosis," describes an ankle and foot orthosis including a series of laterally disposed straps which extend over the top of the foot and about the ankle. A rearwardly disposed ankle support extends downwardly and forwardly to form a plantar foot support, with the ankle and foot support portions comprising a single, monolithic structure with neither component being separable from the other. A bottom sole plate extends beneath and generally parallel to the plantar support portion of the device. The sole plate results in the DeToro assembly being too thick for installation within a shoe or other footwear, whereas the present ankle-foot orthosis is sufficiently thin for wear within a shoe or the like.

U.S. Pat. No. 5,887,591 issued on Mar. 30, 1999 to Mark W. Powell et al., titled "Restraint And Method For The Improved Treatment Of Recalcitrant Plantar Fasciitis," describes various embodiments of an ankle-foot orthosis. One embodiment comprises a rigid, monolithic ankle and plantar portion, formed as a single, unitary component. The forward end includes a removable wedge to provide toe dorsiflexion, but the plantar support portion cannot be removed from the ankle brace portion of the device. Moreover, the sole portion is relatively thick, precluding installation in a shoe or the like.

U.S. Pat. No. 5,944,679 issued on Aug. 31, 1999 to William W. DeToro, titled "Adjustable Ankle And Foot Orthosis Brace," describes a device closely resembling the brace described and illustrated in the '383 U.S. Patent to the same inventor, described further above. The same points raised in the discussion of the '383 U.S. Patent, are seen to apply here as well.

U.S. Pat. No. 6,146,344 issued on Nov. 14, 2000 to Wade Bader, titled "Lower Limb Orthotic Brace," describes a rigid ankle and foot support device formed as a unitary, monolithic component. The device includes reinforcement comprising a relatively thick, tubular braid formed of fiber material, much like a braided rope, and impregnated with a resin or the like for rigidity. This results in a thickness too great for wearing within footwear.

U.S. Pat. No. 6,409,695 issued on Jun. 25, 2002 to John D. Connelly, titled "Ankle-Foot Orthotic," describes a device having a calf or ankle component and foot component connected by lateral pivots at the ankle joint. Only a single attachment strap is disclosed, across the shin of the wearer at the top of the ankle or calf component. The hinged structure does not prevent plantar flexion of the foot, as does the structure of the present invention. Only lateral flexion of the ankle is restricted by the hinge arrangement of the Connelly device. Moreover, the hinged or pivoted attachment of the two components, restricts their separation from one another for different purposes, as provided by the present ankle-foot orthosis invention.

British Patent Publication No. 2,101,894 published on Jan. 26, 1983 to Gerard Molssonnier, titled "Device Permitting The Control Of The Flexion Of A Defective Limb Of A Handicapped Person Fitted With An Orthopaedic Appliance For Its Support And Articulation," describes a leg brace extending from the thigh to a strap which passes beneath the heel. A pivot is provided at the knee joint, with attachment straps about the thigh, calf, and above the ankle. The '894 British Patent Publication is primarily directed to the specifics of the knee hinge mechanism. No removable plantar plate or support is disclosed in the '894 British Patent Publication.

Finally, European Patent Publication No. 195,186 published on Sep. 9, 1986 to Antonietta M. Meola, titled "Stabilizing Orthesis," describes various embodiments of a rigid structure intended to provide support for a paraplegic person. Each of the embodiments includes a wedge-shaped sole with some form of leg brace extending upwardly therefrom. Only one embodiment includes any form of attachment straps, with this embodiment forming a rigid, boot-like enclosure of the foot, ankle, and calf. No removable foot orthosis is provided by Meola, and the device is incapable of being fitted into footwear due to the thickness of the heel portion of the sole.

None of the above inventions and patents, taken either singly or in combination, is seen to describe the instant invention as claimed. Thus a modular ankle-foot orthosis solving the aforementioned problems is desired.

SUMMARY OF THE INVENTION

The present invention comprises a series of embodiments of a modular ankle and foot orthosis in which the lower leg and ankle component and the plantar support component may be quickly and easily disassembled from or reassembled with one another, as required. The present orthotic allows a patient to wear both components assembled together to provide the required support and limit adverse motion of the ankle and foot as required, e.g. for treatment of plantar fasciitis, Achilles tendonitis or post-surgical repair, etc. The lower leg and ankle brace portion may be separated from the plantar support plate and the plantar support worn separately, according to the needs of the patient.

The lower leg and ankle support component of the present assembly includes a forwardly extending heel support portion formed integrally therewith. The heel portion of the plantar support component fits atop and attaches removably to the heel support portion of the lower leg and ankle support component. Various attachment means or mechanisms may be used for removably securing the heel portion of the plantar support component to the heel support portion of the lower leg and ankle support component, e.g., conventional hook and loop fastening material (Velcro®), snap fasteners, etc.

One such attachment means comprises a bottom heel clip extending from the plantar support portion of the present orthosis assembly, with the clip including a rearwardly extending tongue. The clip fits closely within a passage formed in the lower heel portion of the lower leg and ankle support component of the assembly, with the material of the lower leg and ankle support component immediately behind the lower heel passage, being captured between the tongue of the clip and the overlying plantar support structure to secure the plantar support component to the lower leg and ankle support component. This attachment structure provides secure attachment for the two components, yet allows some limited dorsiflexion (reduction of angle between foot and shin) during the "heel off" portion of the stride while walking.

The lower heel portion of the lower leg and ankle support component and the plantar support component are each relatively thin. The clip or other structure used to attach the plantar support to the lower leg and ankle support is also relatively thin, with the relatively low thickness of the assembly allowing the assembly to be worn within a conventional walking shoe or the like. Where only the plantar support portion is to be worn, a heel support attachment may be secured to the clip extending from beneath the heel of the plantar support, to provide a wider base and greater stability.

Accordingly, it is a principal object of the invention to provide a modular ankle-foot orthosis having a lower leg and ankle support portion and a plantar foot support portion which may be quickly and easily secured together or disassembled from one another, as required.

It is another object of the invention to provide a modular ankle-foot orthosis wherein the plantar foot support portion provides limited articulation relative to the lower leg and ankle support portion, particularly during the "heel off" phase of a walking stride.

It is a further object of the invention to provide a modular ankle-foot orthosis with a plantar support portion and a lower leg and ankle support portion which include a bottom heel clip having a tongue extending from the plantar support plate, with the clip and tongue engaging a closely fitting passage within the heel of the lower leg and ankle support portion.

Still another object of the invention is to provide a modular ankle-foot orthosis wherein the plantar support component may be worn separately, as required, or the two components may be assembled together for greater support as required.

An additional object of the invention is to provide a modular ankle-foot orthosis which is sufficiently thin to provide for wearing within a conventional walking shoe or the like, and which further includes a support clip which may be secured to the clip of the plantar support portion to provide a wider base at the heel of the device, thereby providing greater lateral stability and reducing or precluding lateral rocking of the heel while walking or standing.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 3 is a right side elevation view in section of the present modular ankle-foot orthosis assembly, showing its installation within a conventional walking shoe or the like.

Similar reference characters denote corresponding features consistently throughout the attached drawings.

DETAILED DESCRIPTION OF THE PREFERRED EMBODIMENTS

The present invention comprises a series of embodiments of a modular ankle and foot orthosis, for treatment of various problems relating to the feet and/or ankles. The present modular orthosis includes a lower leg and ankle support component and a plantar foot orthotic component, with the two components being quickly and easily assembled to or disassembled from one another, as required. The foot orthotic component may include a heel attachment to broaden the heel support area, for greater lateral stability when using the foot component without the ankle brace.

Figure 1:
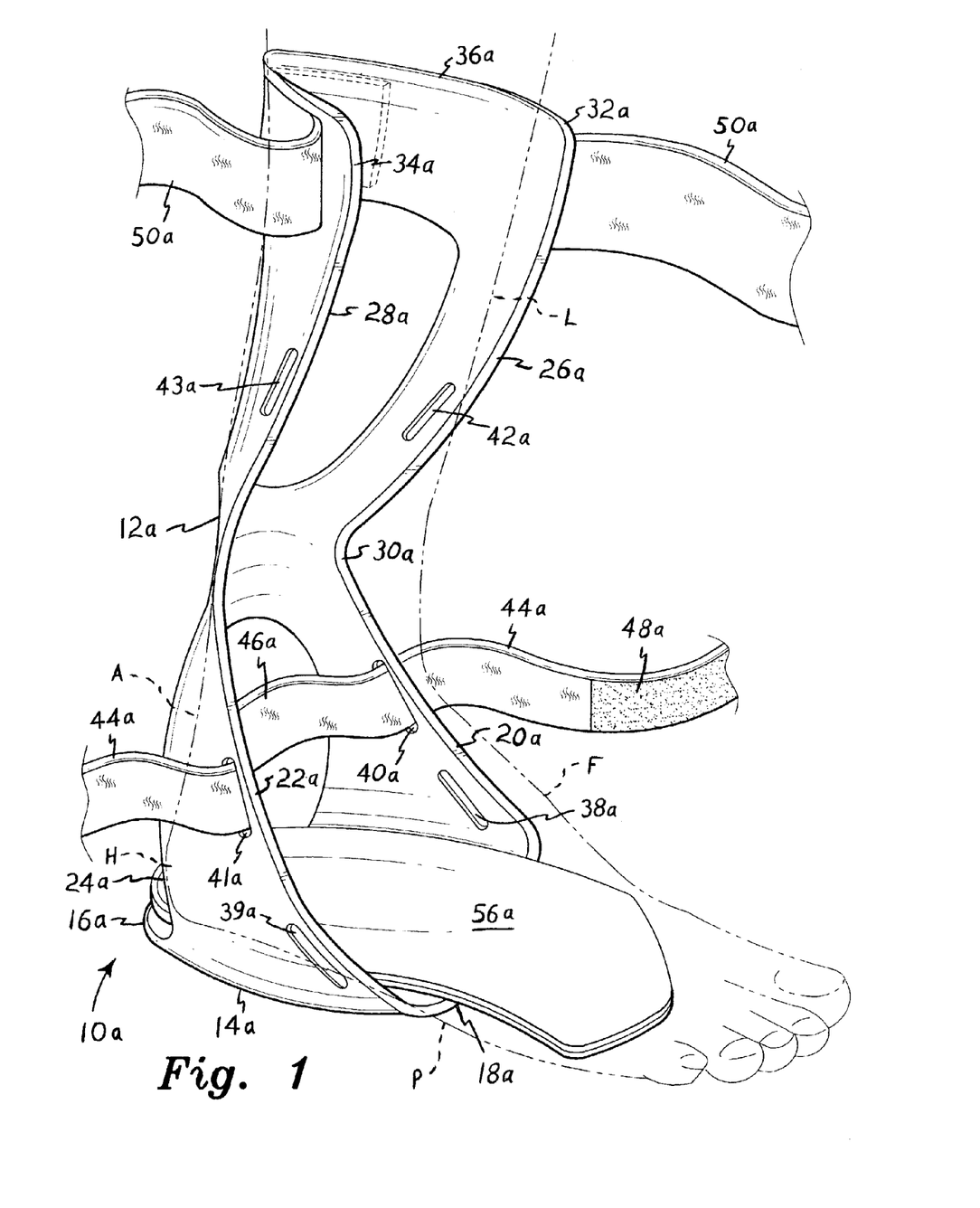
FIG. 1 is a perspective view of a first embodiment of the modular ankle-foot orthosis according to the present invention, showing its various features.

FIG. 1 illustrates a first embodiment of the present modular ankle and foot orthosis assembly, designated by the reference character 10a. The orthosis 10a is separable into two basic components, as noted above. The larger component comprises a lower leg and/or ankle support or brace 12a. preferably formed as a unitary, monolithic structure of a thin, lightweight, and somewhat flexible plastic material (e.g., polypropylene, Nylon®, etc.). The lower leg and ankle component 12a includes a rear foot support plate portion 14a, which resides beneath the heel H or rear foot portion of a patient using the present invention. The lower leg L, foot F, ankle area A, heel H, and plantar or sole portion P of the foot F of a patient or other person wearing or using the present orthosis, are illustrated in broken lines in FIGS. 1 and 3 of the drawings. The rear foot or heel support portion 14a is relatively short, with the rearward end 16a residing beneath or slightly rearwardly of the extreme rearward end of the heel H of the patient, and the opposite forward end 18a extending only to about the forward portion of the heel area H of the patient. However, it will be seen that the rear foot support portion may be extended farther forward to lie beneath a larger percentage of the foot F, if so desired.

A left side and right side ankle support, respectively 20a and 22a, extend upwardly from the rear foot or heel support plate 14a, with the ankle supports 20a and 22a being formed integrally with the heel support plate 14a and immovably affixed thereto. The two ankle support portions 20a and 22a are joined at their upper ends to define a heel clearance opening 24a therebetween, with a left and a right lower leg support, respectively 26a and 28a, extending upwardly from the ankle support upper end joint 30a and integrally formed therewith. Each of the two lower leg supports 26a and 28a has an upper end, respectively 32a and 34a, with a semicircular rear leg band 36a immovably affixed to and formed integrally with the two lower leg supports 26a and 28a, and connecting their upper ends 32a and 34a together.

The modular ankle-foot orthosis 10a of FIG. 1 includes a series of strap attachment slots therein, to provide versatility in the attachment of the orthosis 10a to the lower leg, ankle, and foot of a patient wearing the device. The orthosis 10a of FIG. 1 includes lowermost left and right strap attachment slots 38a, 39a; a pair of ankle attachment strap slots 40a, 41a; and a pair of lower leg or shin strap attachment slots 42a, 43a. An attachment strap, e.g., the ankle attachment strap 44a shown in FIG. 1, may be passed through any of the slot pairs as desired, e.g., the ankle attachment strap slots 40a and 41a, to assist in securing the device to the lower leg, ankle, and foot of the patient. The medial portion 46a of the strap 44a passes behind the heel H of the patient, with the two ends of the strap 44a having conventional attachment means (e.g., hook and loop, Velcro® 48a, etc.) to secure the two ends together. It will be seen that the strap 44a may be inserted through any of the slot pairs 38a, 39a; 40a, 41a; or 42a, 43a, as desired, with multiple straps being used through the several pairs of slots, if so desired. The uppermost end of the device, i.e., the semicircular rear leg band 36a, includes a lower leg attachment strap 50a permanently affixed thereto, with the opposite ends of the strap 50a securing about the shin of the patient using conventional means similar or identical to the means used for attaching the ends of the lower strap 44a to one another.

Figure 2:
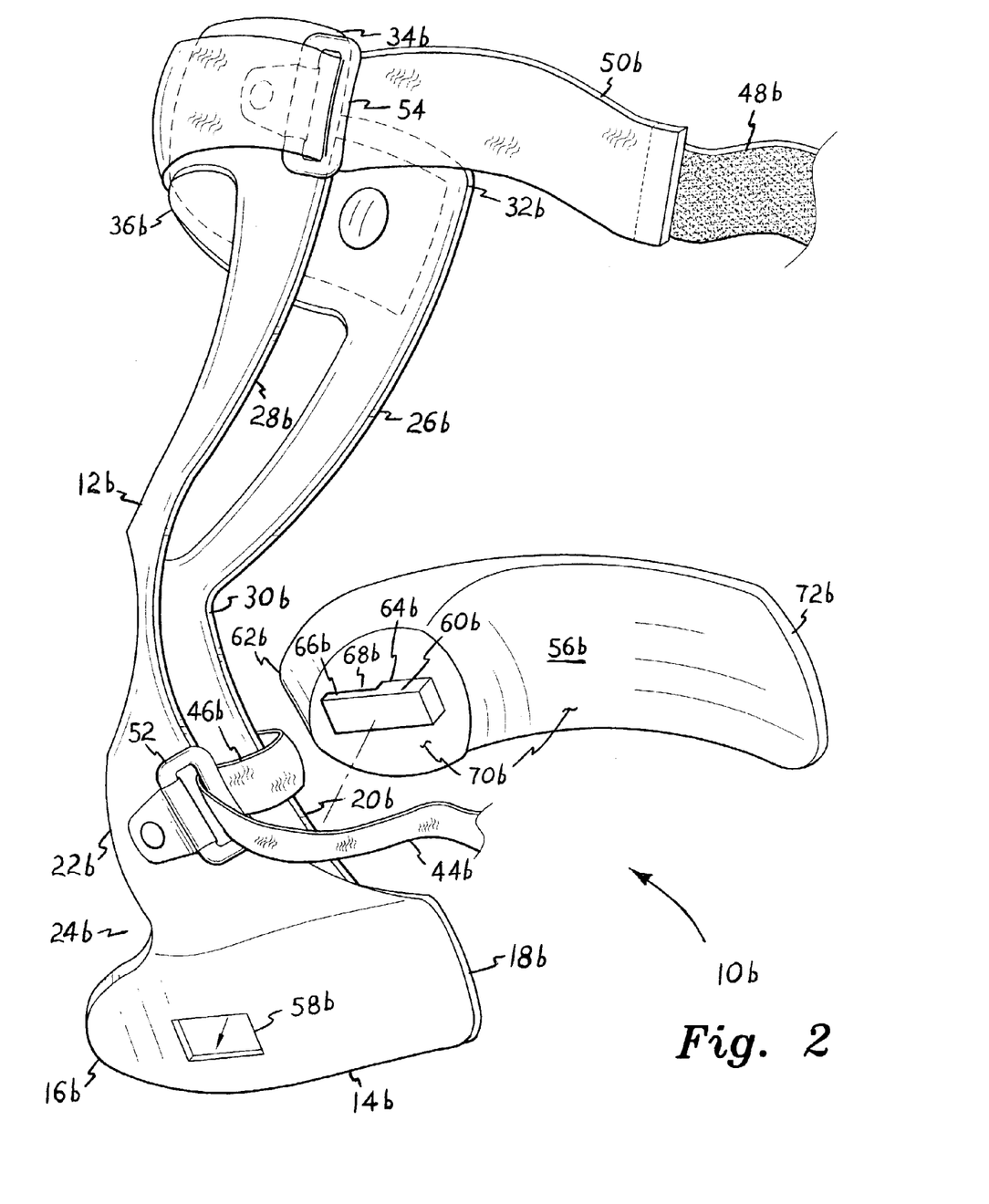
FIG. 2 is an exploded perspective view of a second embodiment of the present modular ankle-foot orthosis having a different attachment strap configuration from the embodiment of FIG. 1, showing the attachment of the plantar support plate to the lower leg and ankle support component.

FIG. 2 is an exploded, bottom and right side perspective view of a second embodiment of the present modular ankle-foot orthosis, designated as orthosis assembly 10b. The orthosis 10b of FIG. 2 differs from the orthosis 10a of FIG. 1, primarily in the arrangement of the lower leg, ankle and foot attachment straps. The rear foot support plate 14b of the orthosis 10b of FIG. 2 is also slightly longer than the short support plate 14a of the orthosis 10a of FIG. 1, but the rear foot support plate may be formed to any practicable length as required, depending upon the specific treatment to be applied by the device. Otherwise, the orthosis 10b of FIG. 2 is essentially identical to the orthosis 10a of FIG. 1, with corresponding components 12 through 36 being designated by a letter "b" suffix (i.e., 12b, 14b, etc.), rather than the letter "a" suffix used in describing the components of the orthosis 10a of FIG. 1.

Rather than providing a series of strap attachment slots, as in the orthosis 10a of FIG. 1, the orthosis 10b of FIG. 2 utilizes a single, lower strap 44b which is permanently secured to one of the ankle supports, e.g., the left side 20b. The lower strap 44b has a medial portion 46b which extends behind the heel of a person wearing the orthosis 10b, to pass through a strap retaining loop 52 secured to the opposite ankle support, e.g., right side ankle support 22b, to be passed back across the front of the ankle and secured by a releasable fastener (e.g., hook and loop, Velcro®, etc.). The upper attachment strap 50b secures to one of the upper ends of the lower leg supports 26b or 28b, e.g., the upper end 32b of the left leg support 26b. A similar opposite side or end attachment arrangement is provided for the opposite side of the orthosis 10b as for the lower strap 44b, with an upper strap retaining loop 54 being attached to the opposite leg support end 34b from the strap anchor attachment on the leg support end 32b. The upper strap 50b may be routed around the back of the rear leg band 36b and through the retaining loop 54, and secured back to itself using Velcro® 48b or other attachment means as desired.

FIG. 2 also illustrates details of one means of removably attaching the plantar foot support 56b to the lower leg and ankle brace 12b. It should be noted that the specific means of attaching the two components 12b and 56b to one another is not critical to the present invention, so long as the aft or heel portion of the plantar foot support 56b secures atop the rear foot or heel support portion of the lower leg and ankle brace component 12b.

One means of removably securing the two components 12b and 56b to one another is illustrated in detail in FIG. 2 of the drawings. It should be noted that while this means is not shown in FIG. 1, such clip (or other) attachment means may be used to secure any of the components of the embodiments of the present orthosis together, as desired. The heel support portion 14b of the ankle and lower leg brace 12b includes a plantar support plate attachment passage 58b formed therethrough, with the passage 58b located near the rearward end 16b of the heel support portion 14b. A corresponding heel bottom support plate clip 60b depends from beneath the plantar support 56b, adjacent the rearward end 62b thereof, and secures removably through the plantar support attachment passage 58b of the heel support portion 14b of the lower leg and ankle support 12b. The base 64b of the heel bottom support plate clip 60b and attachment passage 58b in the heel support portion 14b of the ankle and lower leg brace 12b have mutually congruent configurations (rectangular, etc.). Thus, the plantar support 56b cannot pivot, turn, or otherwise move in an undesired direction while attached to the heel support 14b.

A tongue or extension 66b extends rearward from the support plate clip 60b, and defines a slot 68b between the tongue 66b and the adjacent lower surface 70b of the plantar foot support component 56b. The tongue 66b captures the portion of the heel support 14b adjacent the rearward edge of the plantar support attachment passage 58b formed therethrough, sandwiching that portion of the heel support 14b between the tongue 66b and the underlying lower surface 70b of the plantar foot support 56b, to lock the foot support 56b securely and substantially immovably, but removably, to the heel support 14b. The forward portion and forward end 72b of the plantar foot support 56b, extends forward of the forward edge 18b of the heel support plate 14b to which it is removably attached, although not extending to the full length of the foot, thereby providing additional support for the patient using the present orthosis. The foot support portion 56b is quickly and easily removed from the lower leg and ankle support portion 12b of the assembly, merely by lifting the extended forward end 72b of the foot support plate 56b relative to the heel support portion 14b of the lower leg and ankle support component 12b. This disengages the leading edge of the base 64b of the heel bottom support plate clip 60b from the attachment passage 58b, allowing the plantar foot brace component 56b to be drawn upwardly and forwardly relative to the heel support plate 14b to disengage the tongue 66b of the clip 60b from the heel support 14b.

Figure 3:
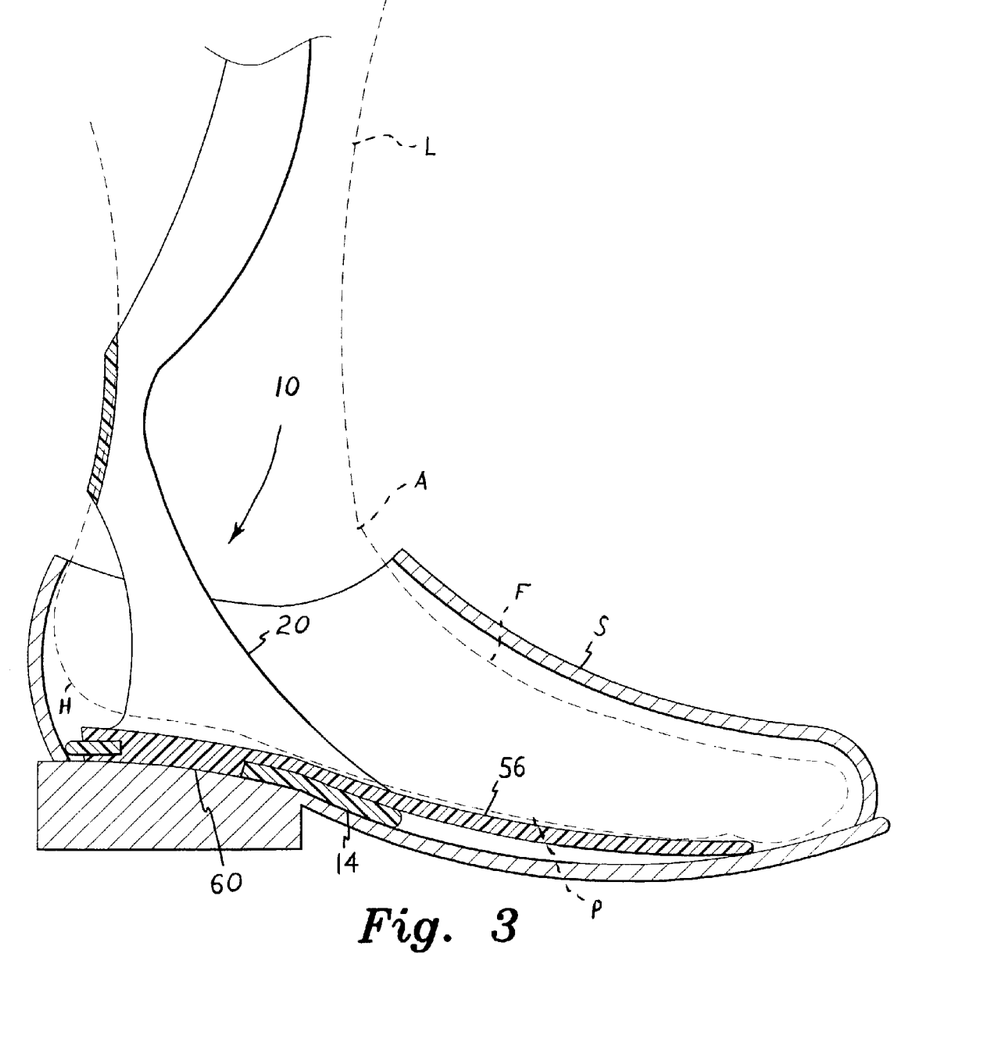

FIG. 3 provides an elevation view in section of a generic ankle and foot orthosis 10 according to the present invention. (It will be seen that attachment straps may be applied to the orthosis 10 of FIG. 3 as desired, resulting in the orthosis 10a of FIG. 1 or orthosis 10b of FIG. 2, or some hybrid or combination thereof.) In FIG. 3, the patient has donned a shoe S over his or her foot F, with the lower end components of the orthosis 10, i.e., the lower portion of the left ankle support 20, heel support plate 14, and plantar support plate 56 with its clip 60 securing the plate 56 to the heel support plate 14, contained within the shoe S. The relative thinness of the components comprising the present orthosis, even when assembled, allows the assembly to be worn by the patient at all times, including during normal activities where shoes are desired or required.

Figure 4:
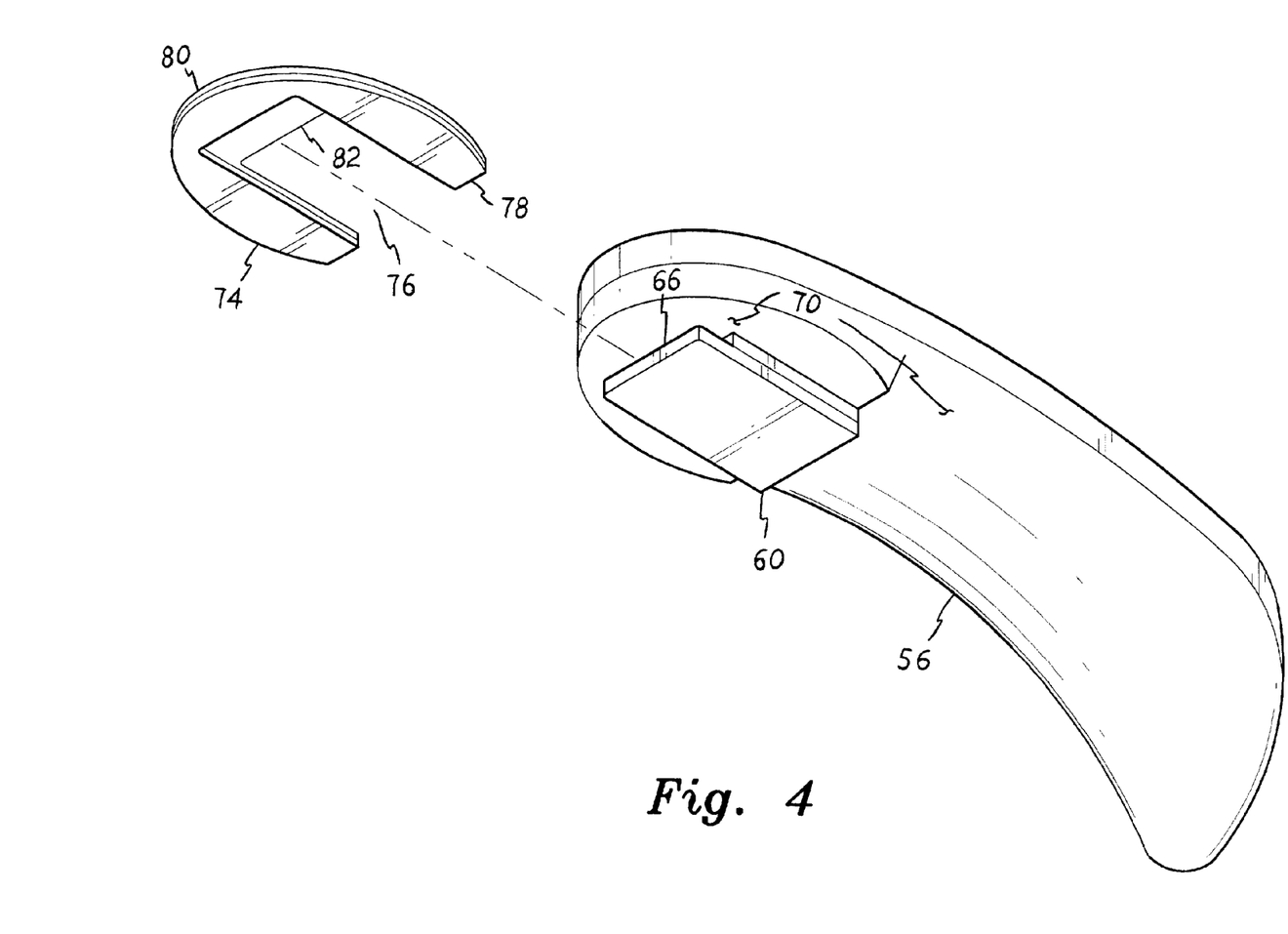
FIG. 4 is a bottom right side perspective view of the plantar support portion of the present invention, showing the removable attachment of a heel support piece thereto.

FIG. 4 provides a bottom and right side perspective view of an exemplary plantar support plate 56, and a stabilizing attachment therefor. The modular nature of the present orthosis in its various embodiments enables a patient to wear only the plantar support component 56, if so desired. The plantar support plate 56, 56a, 56b is made from a strong, thermoplastic material having sufficient rigidity to restrict both dorsiflexion and forefoot plantar flexion when clipped to the lower leg and ankle support brace or strapped to the ankle, while the clip and leg portion are slightly pliable in order to permit some limited dorsiflexion at heel off when walking. Preferably the plantar support plate 56, 56a, 56b, is made from polypropylene, or similar material.

It will be noted that the attachment clip 60 depending from the rear portion of the plantar support 56, is relatively narrow. This could result in some lateral instability for a person wearing the plantar support 56 alone, without the relatively wide heel support portion 14 of the lower leg and ankle support component to provide a wider base. Accordingly, a relatively wide heel support attachment 74 may be provided with the present orthosis, for removable attachment to the clip 60 to enhance the lateral stability of the plantar support 56 when it is worn without the lower leg and ankle component. The heel support attachment 74 includes a slot 76 formed therein, extending from its forward edge 78 to a point near the opposite rearward edge 80 and congruent with the configuration of the clip 60. A relatively thin shelf portion 82 of the heel support attachment 74, somewhat analogous to the portion of the heel support adjacent the rear of the plantar support attachment clip passage 58b shown in FIG. 2, fits between the tongue 66 of the clip 60 and the overlying lower surface 70 of the plantar support plate 56. The heel support attachment 74 is quickly and easily secured to the clip 60 of the plantar support 56, by sliding the attachment 74 forwardly onto the clip until the shelf portion 82 is captured between the tongue 66 of the clip 60 and the overlying surface 70 of the plantar support 56. Removal is just as quickly and easily accomplished, by sliding the attachment 74 rearward from the clip 60. The heel support attachment 74 is of course not required, where other means of removably attaching the heel portion of the plantar support to the underlying heel support portion of the lower leg and ankle brace.

Figure 5:
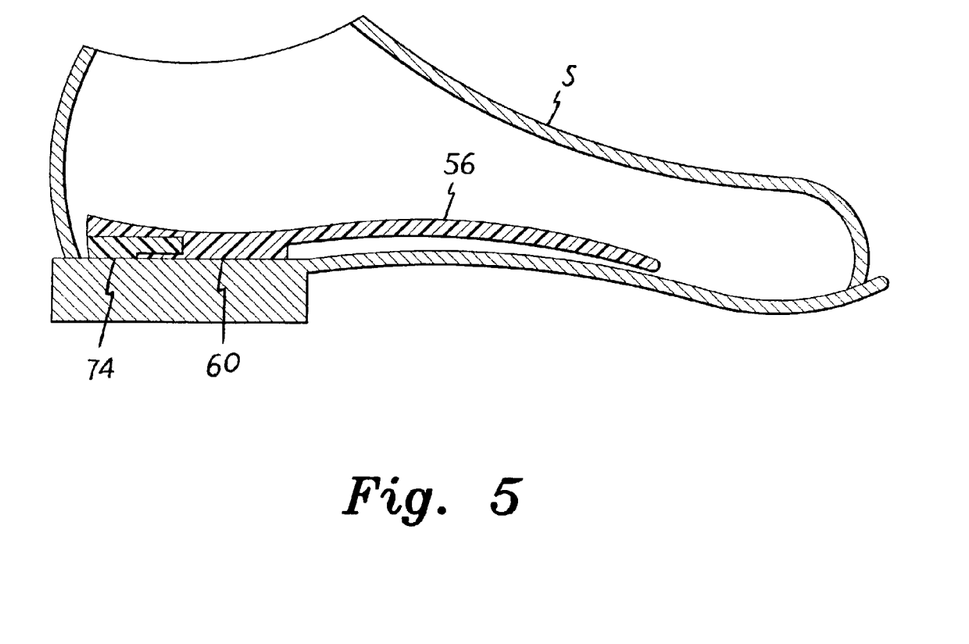
FIG. 5 is a right side elevation view in section of the plantar support plate of the present invention, placed within a conventional shoe with the heel support piece of FIG. 4 installed therewith, showing the additional support provided by the heel support piece.

FIG. 5 is a right side elevation view in section similar to FIG. 3, but without the lower leg and ankle support component. It will be seen that the heel support attachment 74 is installed upon the clip 60 depending from the rearward portion of the plantar support 56, to enhance the lateral stability of the support 56 when the lower leg and ankle support component is not used therewith. The relatively thin nature of the assembly allows it to be worn easily and comfortably within a shoe S. generally as shown in FIG. 5.

In conclusion, the present modular ankle-foot orthosis in its various embodiments, provides much greater versatility in the treatment of various lower leg, ankle, and/or foot ailments. The present orthosis is quite useful in the treatment of plantar fasciitis, where the fascial sheath has become inflamed. The present orthosis may be applied and worn day and night, due to its ability to fit within a conventional shoe. As treatment progresses, the lower leg and ankle brace component may be removed, with the patient utilizing only the plantar orthotic (preferably custom fit to the patient) for further treatment. The present modular orthosis is also of great value in the treatment of Achilles tendonitis and in post-surgical repair of such problems. The present orthosis serves to limit dorsiflexion (movement of the toe upwardly, or toward the front of the body), thereby reducing tensile stresses upon the Achilles tendon. The present modular orthosis is also of value in the treatment of various grades of posterior tibial tendon dysfunction, as well, serving to couple leg and calcaneal (heel) movement by means of the lower leg and ankle component of the assembly. The patient may use either the full brace or only the plantar support portion, depending upon the degree of injury, scope of treatment, and other variables. Certain types of "dropfoot" (e.g., Charcot-Marie-Tooth disease) also respond to treatment using the present modular orthosis. The present orthosis, with its great versatility and low profile, enables the podiatrist or other medical professional to greatly simplify the treatment of various ailments and injuries, without resorting to a large number of cumbersome devices as required conventionally. The resulting convenience and economy will be greatly appreciated by both the medical professional and patient alike.

It is to be understood that the present invention is not limited to the embodiments described above, but encompasses any and all embodiments within the scope of the following claims.

We claim:

1. A modular ankle-foot orthosis for wearing within a shoe and for supporting the ankle, heel, and foot arch of a patient, comprising:
   a lower leg and ankle support brace having:
   a rear foot support plate with a rearward end and a forward end opposite said rearward end;
   a left and a right ankle support extending upwardly from said rear foot support plate, formed integrally and monolithically therewith and immovably affixed thereto;
   a left and a right lower leg support extending upwardly from said left and right ankle support, formed integrally and monolithically therewith and immovably affixed thereto,
   each said lower leg support having an upper end; and
   a semicircular rear leg band connecting the upper ends of said left and said right lower leg support, formed integrally and monolithically therewith and immovably affixed thereto;
   an elongate plantar foot support removably secured to the rear foot support plate of said lower leg and ankle support brace, said plantar foot support having a rearward end and a forward end opposite said rearward end; and
   attachment means for removably securing the rearward end of said plantar foot support atop said rear foot support plate of said lower leg and ankle support brace.

2. The modular ankle-foot orthosis according to claim 1, wherein the rear foot support plate of said lower leg and ankle brace has a plantar support plate attachment passage formed therethrough, adjacent the rearward end thereof, said attachment means comprising:
   a heel bottom support plate clip depending from said plantar foot support adjacent the rearward end thereof, the clip being inserted through the plantar support plate attachment passage of said rear foot support plate.

3. The modular ankle-foot orthosis according to claim 2, further including:
   a tongue extending rearwardly from said rear foot support plate clip of said plantar foot support; and
   the plantar support plate attachment passage of said rear foot support plate and said rear foot support plate clip of said plantar foot support having mutually congruent configurations; whereby
   said rear foot support plate clip of said plantar foot support fits closely within the plantar support plate attachment passage of said rear foot support plate, with said tongue of said rear foot support plate clip capturing a portion of said rear foot support plate between said tongue and said plantar foot support to secure said plantar foot support removably to said rear foot support plate of said lower leg and ankle support.

4. The modular ankle-foot orthosis according to claim 2, further including:

a tongue extending rearwardly from said rear foot support plate clip of said plantar foot support;

a wide, heel support attachment having a slot therein for removably attaching to said rear foot support plate clip of said plantar foot support;

said slot of said heel support attachment and said rear foot support plate clip of said plantar foot support having mutually congruent configurations; whereby said rear foot support plate clip of said plantar foot support fits closely within said slot of said heel support attachment with said tongue of said rear foot support plate clip capturing a portion of said heel support attachment between said tongue and said plantar foot support to secure said heel support attachment removably to said plantar foot support, thereby providing a wide heel support and increasing lateral stability of said plantar foot support and said heel support attachment when assembled together.

5. The modular ankle-foot orthosis according to claim 1, wherein said rear foot support plate has a short length, with said forward end thereof being adapted for terminating generally beneath the forward portion of the heel of the patient when said lower leg and ankle support component is being worn by the patient.

6. The modular ankle-foot orthosis according to claim 1, further including:
a plurality of strap attachment slots disposed along said left and said right lower leg support and said left and said right ankle support of said lower leg and ankle support component;
at least one lower leg attachment strap extending from said rear leg band of said lower leg and ankle support component; and
at least one ankle attachment strap extending from said left and said right ankle support of said lower leg and ankle support component.

7. The modular ankle-foot orthosis according to claim 1, further including at least one strap loop extending from said rear leg band of said lower leg and ankle support component and from one of said left and said right ankle support of said lower leg and ankle support component.

8. A lower leg orthosis for wearing within a shoe and for supporting the ankle and heel of a patient, comprising:
a short rear foot support plate having a rearward end and a forward end opposite said rearward end, said rear foot support plate having a short length, with the forward end thereof being adapted for terminating generally beneath the forward portion of the heel of the patient, said rear foot support plate being adapted for attachment of a plantar support plate;
a left and a right ankle support extending upwardly from said rear foot support plate, formed integrally and monolithically therewith and immovably affixed thereto;
a left and a right lower leg support extending upwardly from said left and right ankle support, formed integrally and monolithically therewith and immovably affixed thereto, each said lower leg support having an upper end; and
a semicircular rear leg band connecting the upper ends of said left and said right lower leg supports, formed integrally and monolithically therewith and immovably affixed thereto.

9. The lower leg orthosis according to claim 8, wherein said rear foot support plate has a plantar support plate attachment passage defined therein, the orthosis further including:

an elongate plantar foot support removably secured to said rear foot support plate of said lower leg and ankle support component, said plantar foot support having a rearward end and a forward end opposite said rearward end; and a rear foot support plate clip depending from said plantar foot support adjacent said rearward end thereof, for removably securing through said plantar support plate attachment passage of said rear foot support plate.

10. The lower leg orthosis according to claim 9, further including:
a tongue extending rearwardly from said rear foot support plate clip of said plantar foot support;
said plantar support plate attachment passage of said rear foot support plate and said rear foot support plate clip of said plantar foot support having mutually congruent configurations; whereby
said rear foot support plate clip of said plantar foot support fits closely within said plantar support plate attachment passage of said rear foot support plate, with said tongue of said rear foot support plate clip capturing a portion of said rear foot support plate between said tongue and said plantar foot support to secure said plantar foot support removably to said rear foot support plate of said lower leg and ankle support.

11. The lower leg orthosis according to claim 9, further including:
a tongue extending rearwardly from said rear foot support plate clip of said plantar foot support;
a wide, heel support attachment having a slot therein for removably attaching to said rear foot support plate clip of said plantar foot support;
said slot of said heel support attachment and said rear foot support plate clip of said plantar foot support having mutually congruent configurations; whereby
said rear foot support plate clip of said plantar foot support fits closely within said slot of said heel support attachment with said tongue of said rear foot support plate clip capturing a portion of said heel support attachment between said tongue and said plantar foot support to secure said heel support attachment removably to said plantar foot support, thereby providing a wide heel support and increasing lateral stability of said plantar foot support and said heel support attachment when assembled together.

12. The lower leg orthosis according to claim 8, further including:
a plurality of strap attachment slots disposed along said left and said right lower leg support and said left and said right ankle support of said lower leg and ankle support component;
at least one lower leg attachment strap extending from said rear leg band of said lower leg and ankle support component; and
at least one ankle attachment strap extending from said left and said right ankle support of said lower leg and ankle support component.

13. The lower leg orthosis according to claim 8, further including at least one strap loop extending from said rear leg band of said lower leg and ankle support component and from one of said left and said right ankle support of said lower leg and ankle support component.

14. A foot orthosis for wearing within a shoe and for supporting the foot arch of a patient, comprising:
an elongate plantar foot support having a rearward end and a forward end opposite said rearward end;

attachment means for attaching said plantar foot support to a rear foot support plate;

said attachment means comprising a rear foot support plate clip having a tongue extending rearwardly;

a wide, heel support attachment having a slot defined therein for removably attaching to said rear foot support plate clip of said plantar foot support;

said slot of said heel support attachment and said rear foot support plate clip of said plantar foot support having mutually congruent configurations; whereby said rear foot support plate clip of said plantar foot support fits closely within said slot of said heel support attachment with said tongue of said rear foot support plate clip capturing a portion of said heel support attachment between said tongue and said plantar foot support to secure said heel support attachment removably to said plantar foot support, thereby providing a wide heel support and increasing lateral stability of said plantar foot support and said heel support attachment when assembled together.

15. A foot orthosis for wearing within a shoe and for supporting the foot arch of a patient, comprising:

an elongate plantar foot support having a rearward end and a forward end opposite said rearward end;

attachment means for attaching said plantar foot support to a rear foot support plate;

a lower leg and ankle support component having a rear foot support plate with a rearward end and a forward end opposite said rearward end, said rear foot support plate having a plantar support plate attachment passage formed therethrough;

a left and a right ankle support extending upwardly from said rear foot support plate, formed integrally and monolithically therewith and immovably affixed thereto;

a left and a right lower leg support extending upwardly from said left and right ankle support, formed integrally and monolithically therewith and immovably affixed thereto;

each said lower leg support having an upper end;

a semicircular rear leg band connecting said upper end of said left and said right lower leg support, formed integrally and monolithically therewith and immovably affixed thereto; and wherein said attachment means comprises a clip depending from said plantar support plate, said clip mating with the passage defined in said rear foot support plate.

16. The foot orthosis according to claim 15, wherein said rear foot support plate of said lower leg and ankle support component has a short length, with said forward end thereof terminating generally beneath the forward portion of the heel of the patient when said lower leg and ankle support component is being worn by the patient.

17. The foot orthosis according to claim 15, further including:

a tongue extending rearwardly from said rear foot support plate clip of said plantar foot support; and said plantar support plate attachment passage of said rear foot support plate and said rear foot support plate clip of said plantar foot support having mutually congruent configurations; whereby said rear foot support plate clip of said plantar foot support fits closely within said plantar support plate attachment passage of said rear foot support plate, with said tongue of said rear foot support plate clip capturing a portion of said rear foot support plate between said tongue and said plantar foot support to secure said plantar foot support removably to said rear foot support plate of said lower leg and ankle support.

18. The foot orthosis according to claim 15, further including:

a plurality of strap attachment slots disposed along said left and said right lower leg support and said left and said right ankle support of said lower leg and ankle support component;

at least one lower leg attachment strap extending from said rear leg band of said lower leg and ankle support component; and at least one ankle attachment strap extending from said left and said right ankle support of said lower leg and ankle support component.

19. The foot orthosis according to claim 15, further including at least one strap loop extending from said rear leg band of said lower leg and ankle support component and from one of said left and said right ankle support of said lower leg and ankle support component.

* * * * *